(12) United States Patent
Sauter et al.

(10) Patent No.: US 6,652,601 B2
(45) Date of Patent: Nov. 25, 2003

(54) AGENT FOR DYEING FIBERS COMPRISING AN INDOLINE/INDOLIUM DERIVATIVE

(75) Inventors: Guido Sauter, Marly (CH); Hans-Juergen Braun, Ueberstorf (CH); Nadia Reichlin, Cugy (CH)

(73) Assignee: Wella Aktiengesellschaft, Darmstadt (DE)

( * ) Notice: Subject to any disclaimer, the term of this patent is extended or adjusted under 35 U.S.C. 154(b) by 213 days.

(21) Appl. No.: 09/959,112

(22) PCT Filed: Jan. 25, 2001

(86) PCT No.: PCT/EP01/00821
§ 371 (c)(1),
(2), (4) Date: Oct. 17, 2001

(87) PCT Pub. No.: WO01/62219
PCT Pub. Date: Aug. 30, 2001

(65) Prior Publication Data
US 2003/0079301 A1 May 1, 2003

(30) Foreign Application Priority Data
Feb. 22, 2000 (DE) .......................... 100 07 948

(51) Int. Cl.[7] .................................. A61K 7/13
(52) U.S. Cl. .............. 8/405; 8/426; 8/102; 8/110; 8/917; 8/918; 8/587; 8/607; 8/608; 8/404
(58) Field of Search .............. 8/404, 405, 426, 8/102, 110, 917, 918, 587, 607, 608

(56) References Cited

U.S. PATENT DOCUMENTS

| | | | |
|---|---|---|---|
| 3,865,837 A | * 2/1975 | Krutak, Sr. | 260/326.11 |
| 4,542,223 A | * 9/1985 | Raue et al. | 548/455 |
| 4,785,097 A | * 11/1988 | Kwak | 544/71 |
| 4,831,142 A | * 5/1989 | Kwak | 544/71 |

FOREIGN PATENT DOCUMENTS

| | | |
|---|---|---|
| DE | 1949 716 | 4/1970 |
| DE | 43 35 623 A1 | 4/1995 |
| DE | 44 09 143 A1 | 9/1995 |
| DE | 197 17 222 A1 | 10/1998 |
| DE | 197 17 280 A1 | 10/1998 |
| DE | 197 45 292 A1 | 4/1999 |
| DE | 299 08 464 U | 9/1999 |
| DE | 198 20 894 A | 11/1999 |
| DE | 199 34 283 A1 | 1/2001 |
| EP | 0 370 492 A | 5/1990 |
| EP | 0 873 746 A | 10/1998 |
| EP | 0 847 749 B1 | 12/1999 |
| WO | 00 33799 A | 6/2000 |
| WO | 00 38639 A | 7/2000 |

OTHER PUBLICATIONS

Dissertation BTY Andreas Leiminer "Chirale Spirooxazine und Spiropyrane . . . ", Universitaet Regensburg, Altdorf/Landshut 1995.

D.J. Gale et al "Fibre–Reative Basic Dyes I–Polymethine Dyes Containing the N–Chloroacetyl Group", In J. Soc. Dyers Colour, Mar. 1974, pp. 97–100.

\* cited by examiner

*Primary Examiner*—Margaret Einsmann
*Assistant Examiner*—Eisa Elhilo
(74) *Attorney, Agent, or Firm*—Michael J. Striker

(57) ABSTRACT

The object of the present invention is an agent for dyeing fibers obtained by mixing two components and characterized in that one component (component A2) contains at least one carbonyl compound and the other component (component A1) contains at least one indoline derivative of formula (I) or a 3H-indoline derivative of formula (Ia)

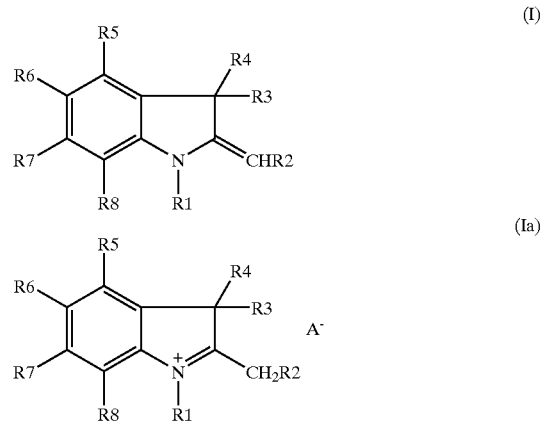

as well as a multicomponent kit for dyeing and later decolorizing fibers, said kit containing both an agent according to the invention for producing a coloration on the fiber and an agent for the reductive removal of said coloration.

10 Claims, No Drawings

AGENT FOR DYEING FIBERS COMPRISING AN INDOLINE/INDOLIUM DERIVATIVE

The object of the present invention is an agent for dyeing fibers, particularly keratin fibers (for example human hair), said agent containing an indole derivative and a carbonyl compound, and to a multicomponent kit for dyeing and subsequently decolorizing fibers, said kit containing both an agent for producing a coloration on the fibers and an agent for the reductive removal of the coloration.

Depending on the starting color of the hair to be dyed and the desired end result, hair colorants fall mainly into the domain of oxidative hair dyes and tinting agents. Oxidative dyes lend themselves eminently to the covering of large gray areas. The oxidative dyes used when the gray area amounts to up to 50% are usually referred to as oxidative tinting agents, whereas the oxidative dyes used when the gray area exceeds 50% or the dyes used for "bright coloring" are usually referred to as oxidative dyes. Direct dyes are contained mainly in non-oxidative colorants (tinting agents). Some direct dyes, for example the nitro dyes, can, because of their small size, penetrate into the hair and—at least in the outer regions—bring about direct dyeing. Such tinting agents are very gentle to the hair, they can usually withstand 6 to 8 hair washings and they allow a gray coverage of about 20%.

In general, direct dyes and oxidative tints are washed out of the hair after a few hair washings. Their durability depends among other things on the hair structure and the color shade used. Oxidative dyes can fade somewhat with time, but as a rule remain on the hair until the next haircut. When it is desired to wear a particular color only for a certain length of time or if the user dislikes a color, however, it may be desirable to be able to remove the hair coloring at any time. Also, when a person's hair is dyed for the first time, a gentle and complete removal of the coloration can reduce the fear of an excessively drastic color change ("test dyeing").

European Patent EP 0 847 749 discloses a combination of diiminoisoindoline or 3-aminoisoindolone derivatives and compounds with primary or secondary amino groups for coloring keratin fibers without the addition of an oxidant. It is also known from German Unexamined Patent Application DE-OS 43 35 623 to use for the dyeing of keratin fibers a combination of indolinone derivatives and compounds with primary or secondary amino groups, heterocycles or aromatic hydroxy compounds. Moreover, DE-OS 44 09 143 describes the use of isatin derivatives for the dyeing of keratin fibers. DE-OS 197 45 292 discloses the use of a combination of malonaldehyde derivatives, for example malonaldehyde-bis-dialkyl acetals, and amines or CH-acidic compounds for dyeing hair without the addition of oxidants. Also, DE-OS 197 17 280 discloses the use of a combination of certain heterocyclic aldehydes and amines or CH-acidic compounds for dyeing hair without the addition of oxidants.

A great demand, however, continues to exist for colorants which under mild conditions give intense as well as gentle colorations in a wide range of shades and which—if desired—can subsequently be removed at any time.

The object of the present invention is therefore to provide a dyeing system which without the addition of an oxidant (for example hydrogen peroxide) gives a gentle, intense coloration on fibers in the yellow, brown, green and purple range with good fastness properties (light fastness, wash fastness, abrasion resistance) and at the same time permits gentle and complete removal of said coloration at any point in time.

Surprisingly, we have now found that dyes containing an indoline derivative of formula (I) or a 3H-indolium derivative of formula (Ia) as well as a carbonyl compound give in gentle manner intense colorations which can be removed completely at any desired subsequent point in time.

Hence, the object of the present invention is an agent for dyeing fibers, for example wool, silk, cotton or hair, and particularly keratinic fibers, for example human hair, said agent being obtained by mixing two components—if necessary with addition of an alkalinizing agent or an acid—and being characterized in that one component (component A2) contains at least one carbonyl compound, particularly an aromatic aldehyde compound, and the other component (component A1) contains at least one indoline derivative of formula (I) or a 3H-indolium derivative of formula (Ia)

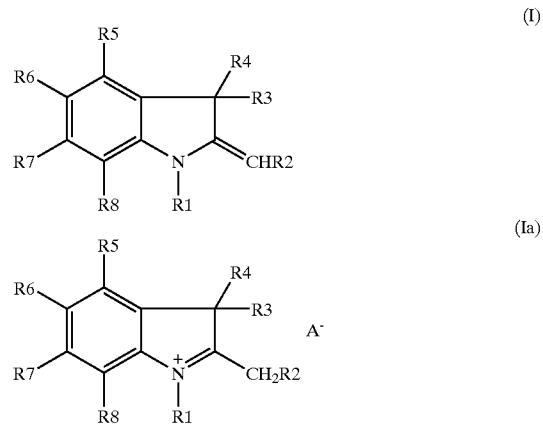

the R1 to R8 and A⁻ groups in formulas (I) and (Ia) having the following meaning:

R1 denotes a straight-chain or branched C1–C8 alkyl group, C1–C8 monohydroxyalkyl group, C2–C8 polyhydroxyalkyl group, C1–C8 alkoxy-(C1–C8)-alkyl group or a thio-(C1–C8)-alkyl group, a —(CH$_2$)$_m$—X—(CH$_2$)$_n$—Y—(CH$_2$)$_p$—R$^a$ group, a —(CH$_2$)$_n$—X—R$^a$ group, a —(CH$_2$)$_m$—Y—(CH$_2$)$_n$—X—(CH$_2$)$_p$—R$^a$ group, a —(CH$_2$)$_m$—CO—(CH$_2$)$_p$—X—R$^a$ group, a —(CH$_2$)$_p$—R$^a$ group, a —(CH$_2$)$_m$—X—(CH$_2$)$_p$—CO—Y—R$^a$ group or

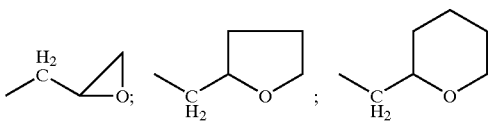

wherein

X and Y independently of each other denote an oxygen atom, a sulfur atom or an NR$^b$ group, R$^a$ and R$^b$ independently of each other denote a hydrogen atom, an, optionally substituted, aromatic carbocycle or heterocycle or a straight-chain or branched C1–C8 alkyl group, m and n independently of each other denote an integer from 1 to 6 and p denotes an integer from 0 to 6;

R2 is a hydrogen atom or a straight-chain C1 to C6-alkyl group,

R3 and R4 independently of each other denote a straight-chain or branched C1–C4-alkyl group (particularly a methyl group), a (CH$_2$)$_n$—R$^c$ group, a —(CH$_2$)$_m$—CHR$^c$—X—(CH$_2$)$_n$—R$^c$ group, a —(CH$_2$)$_n$—CO—R$^c$ group, a —(CH$_2$)$_n$—CO—XR$^c$ group, a (CH$_2$)$_n$—CN group, a —(CH$_2$)$_n$—CH═C(CH$_3$)$_2$ group, a —(CH$_2$)$_m$—X—CHR$^c$—(CH$_2$)$_n$—R$_c$ group or a —(CH$_2$)$_n$CH═CH group, X standing for an oxygen atom, a sulfur atom or an NR$^b$ group, m and n independently of each other denoting 1 to 6 and R$^c$ standing for a hydrogen atom, an, optionally substituted, aromatic carbocycle or heterocycle or a straight-chain or branched C1–C6-alkyl group, providing that the R3 and R4 groups, together, linked through a (CH$_2$)$_n$ group (with n=1–3) can also form a spiro compound with the 3H carbon;

R5, R6, R7 and R8 independently of each other denote a straight-chain or branched C1–C4-alkyl group or a C1–C4-hydroxyalkyl group, a hydroxyl group, a methoxy group, a benzyl group, a halogen atom (F, Cl, Br, I), a nitro group, a nitroso group, a cyano group, a trifluoromethyl group, a —CHO group, a —COR$^d$ group, a —COOH group, a —CO$_2$R$^d$ group, an —OCOR$^d$ group, an —OCH$_2$-aryl group, an —SO$_2$NH$_2$ group, an —NH$_2$ group, an —NH$_3^+$ group, an —NHR$^d$ group, an —NH$_2$R$^{d+}$ group, an —N(R$^d$)$_2$ group, an —N(R$^d$)$_3^+$ group, an —NHCOR$^d$ group, an —NHCOOR$^d$ group, a —CH$_2$NH$_2$ group, a —CH$_2$NHR$^d$ group, a —CH$_2$N(R$^d$)$_2$ group, a —CO$_2$CF$_3$ group, a —PO(OR$^d$)$_2$ group, —SO$_2$CHF$_2$ group, an —SO$_2$CF$_3$ group an —SO$_2$R$^d$ group or an —SR$^d$ group, wherein R$^d$ denotes a hydrogen atom, an, optionally substituted, aromatic carbocycle or a heterocycle or a C1–C6-alkyl group, providing that at least one of the R5 to R8 groups is different from hydrogen; and A$^-$ denotes an anion of an organic or inorganic acid.

A$^-$ is preferably a chloride, bromide, iodide, hydrogen sulfate, sulfate, toluenesulfonate, benzenesulfonate, monomethyl sulfate, hexafluorophosphate, hexafluoroantimonate, tetrafluoroborate, tetraphenylborate, formate, acetate or propionate ion. The chloride ion, tetrafluoroborate ion, acetate ion and hydrogen sulfate ion are particularly preferred.

Among the compounds of formulas (I) and (Ia), the following are preferred:

1,3,3,4-tetramethyl-2-methyleneindoline and the salts thereof,
1,3,3,5-tetramethyl-2-methyleneindoline and the salts thereof,
1,3,3,6-tetramethyl-2-methyleneindoline and the salts thereof,
1,3,3,7-tetramethyl-2-methyleneindoline and the salts thereof,
1,3,3,6,7-pentamethyl-2-methyleneindoline and the salts thereof,
1,3,3,5,7-pentamethyl-2-methyleneindoline and the salts thereof,
1,3,3,4,7-pentamethyl-2-methyleneindoline and the salts thereof,
5-fluoro-1,3,3-trimethyl-2-methyleneindoline and the salts thereof,
5-isopropyl-1,3,3-trimethyl-2-methyleneindoline and the salts thereof,
5-hydroxy-1,3,3-trimethyl-2-methyleneindoline and the salts thereof,
5-methoxy-1,3,3-trimethyl-2-methyleneindoline and the salts thereof,
5-nitro-1,3,3-trimethyl-2-methyleneindoline and the salts thereof,
5-amino-1,3,3-trimethyl-2-methyleneindoline and the salts thereof,
5-N-acetylamino-1,3,3-trimethyl-2-methyleneindoline and the salts thereof,
6-hydroxy-1,3,3-trimethyl-2-methyleneindoline and the salts thereof,
6-methoxy-1,3,3-trimethyl-2-methyleneindoline and the salts thereof,
5-methoxy-6-nitro-1,3,3-trimethyl-2-methyleneindoline and the salts thereof,
5-methoxy-6-amino-1,3,3-trimethyl-2-methyleneindoline and the salts thereof,
5-methoxy-6-N-acetylamino-1,3,3-trimethyl-2-methyleneindoline and the salts thereof,
5,6-dihydroxy-1,3,3-trimethyl-2-methyleneindoline and the salts thereof,
5,6-dimethoxy-1,3,3-trimethyl-2-methyleneindoline and the salts thereof,
5,6-methylenedioxy-1,3,3-trimethyl-2-methyleneindoline and the salts thereof,
4,5-dihydroxy-1,3,3-trimethyl-2-methyleneindoline and the salts thereof,
5,7-dihydroxy-1,3,3-trimethyl-2-methyleneindoline and the salts thereof,
5-amino-6-methoxy-1,3,3-trimethyl-2-methyleneindoline and the salts thereof,
5-amino-7-hydroxy-1,3,3-trimethyl-2-methyleneindoline and the salts thereof,
5-hydroxy-7-amino-1,3,3-trimethyl-2-methyleneindoline and the salts thereof,
5-hydroxy-7-N-acetylamino-1,3,3-trimethyl-2-methyleneindoline and the salts thereof,
1-methyl-3-spirocyclopropyl-2-methyleneindoline and the salts thereof,
1-methyl-3-spirocyclohexyl-2-methyleneindoline and the salts thereof,
1-methyl-3-spirocyclohexyl-5-hydroxy-2-methyleneindoline and the salts thereof,
1-methyl-3-spirocyclohexyl-5-methoxy-2-methyleneindoline and the salts thereof,
the following being particularly preferred:
1,2,3,3,5-pentamethyl-3H-indolium iodide,
1,2,3,3,7-pentamethyl-3H-indolium tetrafluoroborate,
1,2,3,3,6,7-hexamethyl-3H-indolium tetrafluoroborate,
1,2,3,3,5,7-hexamethyl-3H-indolium tetrafluoroborate,
1,2,3,3,4,7-hexamethyl-3H-indolium tetrafluoroborate,
5-fluoro-1,2,3,3-tetramethyl-3H-indolium iodide,
5-isopropyl-1,2,3,3-tetramethyl-3H-indolium iodide,
5-nitro-1,3,3-trimethyl-2-methyleneindoline
and especially
5-methoxy-1,2,3,3-tetramethyl-3H-indolium iodide,
5-methoxy-6-nitro-1,2,3,3-tetramethyl-3H-indolium chloride,
5-hydroxy-1,2,3,3-tetramethyl-3H-indolium iodide and
5-N-acetylamino-1,2,3,3-tetramethyl-3H-indolium acetate.

The compounds of formulas (I) and Ia) used according to the invention are known from the literature or can be prepared by standard methods of synthesis known from the literature, for example such as those described in the dissertation by Andreas Leiminer, University of Regensburg (1995); in the German Unexamined Patent Application [DE-OS] 1 949 716 or in U.S. Pat. No. 3,865,837. By the electrophilic substitution reactions known from the literature, additional, new substituents, for example a nitro function, can be introduced into the aromatic ring. In this respect, the reader is referred particularly to the synthesis method described by D. J. Gale and J. F. K. Wilshire in J. Soc. Dyers Colour; 1974. pp. 97–100. By later treatment with reducing or oxidizing agents or with the aid of appropriate protective group addition or elimination reactions, the functional nature of the introduced substituents can be modified whereby additional compounds of general formulas (I) and (Ia) can be obtained.

Suitable carbonyl compounds are, in particular, the following aldehydes: vanillin (4-hydroxy-3-methoxybenzaldehyde), isovanillin (3-hydroxy-4-methoxybenzaldehyde), 3,4-dihydroxybenzaldehyde, 4-hydroxybenzaldehyde, 3,5-dimethoxy-4-hydroxybenzaldehyde, 4-dimethylaminobenzaldehyde, 4-methyl-5-imidazolecarboxaldehyde, 4-dimethylaminocinnamaldehyde, 4-hydroxy-2-methoxybenzaldehyde, 3,5-dimethyl-4-hydroxybenzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxybiphenyl-1-carboxaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, indole-3-carboxaldehyde, benzene-1,4-dicarboxaldehyde, 4-ethoxybenzaldehyde, 2-methyl-1,4-naphthoquinone, 4-carboxybenzaldehyde, 4-hydroxy-3-methoxycinnamaldehyde, 3,5-dimethoxy-4-hydroxycinnamaldehyde, 3-methoxy-4-(1-pyrrolidinyl) benzaldehyde, 4-diethylamino-3-methoxybenzaldehyde, 1,2,-phthalaldehyde, pyrrole-2-aldehyde, thiophene-2-aldehyde, thiophene-3-aldehyde, chromone-3-carboxaldehyde, 6-methyl-4-oxo-1 (4H)-benzopyran-3-carboxaldehyde, N-methylpyrrole-2-aldehyde, 5-methylfufural, 6-hydroxychromene-3-carboxaldehyde, 6-methylindole-3-carboxaldehyde, 4-dibutylaminobenzaldehyde, N-ethyl-carbazole-3-aldehyde, 4-diethylamino-2-hydroxybenzaldehyde, 3,4-dimethoxy-5-hydroxybenzaldehyde, 5-[4-(diethylamino) phenyl]-2,4-pentadienal, 2,3-thiophenecarboxaldehyde, 2,5-thiophenedicarboxaldehyde, 2-methoxy-1-naphthaldehyde, 3-ethoxy-4-hydroxybenzaldehyde, 2-nitrobenzaldehyde, 3-nitrobenzaldehyde and 4-nitrobenzaldehyde.

The compounds of formulas (I) and (Ia) are kept separated from the carbonyl compounds until shortly before use. As a rule, the colorant of the invention is a mixture of the two components A1 and A2, namely of a dye carrier composition (A1) containing the compounds (I) and/or (Ia) and optionally a direct dye, and an additional dye carrier composition (A2) containing the carbonyl compound and optionally a direct dye. These two components are mixed just before use to give a ready-for-use colorant which is then applied to the fibers to be dyed. One or both components can, of course, also consist of several individual components which are mixed with each other just before use.

The compounds of formulas (I) and (Ia) and the carbonyl compounds are contained in each of the dye carrier compositions (component A1 or component A2) in a total amount from about 0.02 to 20 wt. % and preferably from 0.2 to 10 wt. %, and the ready-for-use colorant obtained by mixing components A1 and A2 contains the compounds of formulas (I) and (Ia) and the carbonyl compound in a total amount from about 0.01 to 10 wt. % and preferably from 0.1 to 5 wt. %.

Moreover, the coloring agent of the invention can optionally contain common physiologically tolerated direct dyes from the group of nitro dyes, azo dyes, quinone dyes and triphenylmethane dyes.

The direct dyes can be contained in each of component A1 and component A2 in a total amount from about 0.2 to 10 wt. % and preferably from about 0.02 to 10 wt. %, the total amount of direct dyes in the ready-for-use colorant obtained by mixing components A1 and A2 being from about 0.01 to 10 wt. % and preferably from 0.1 to 5 wt. %.

The ready-for-use colorant and components A1 and A2 can be prepared in the form of, for example, a solution, particularly an aqueous or aqueous-alcoholic solution. Other suitable forms are creams, gels, aerosol foams or emulsions. The colorant composition is a mixture of the compounds of formulas ID (I) and (Ia) and/or a carbonyl compound with additives commonly used for such preparations.

Common additives used in colorants in the form of a solution, cream, emulsion, gel or aerosol foam are, for example, solvents such as water, lower aliphatic alcohols, for example ethanol, n-propanol and isopropanol, or polyols such as glycerol and 1,2-propanediol, moreover wetting agents or emulsifiers from the classes of anionic, cationic, amphoteric or nonionic surface-active agents, such as fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty esters, furthermore thickeners such as higher fatty alcohols, starch or cellulose derivatives, perfumes, hair pretreatment agents, conditioners, hair swelling agents, preservatives, moreover vaselines, paraffin oils and fatty acids as well as hair-care agents, such as cationic resins, lanolin derivatives, cholesterol, pantothenic acid and betaine. The aforesaid components are used in amounts commonly employed for such purposes, for example the wetting agents and emulsifiers at a concentration of about 0.5 to 30 wt. % (based on the dye carrier composition), the thickeners in an amount of about 0.1 to 25 wt. % (based on the dye carrier composition) and the hair-care agents at a concentration of about 0.1 to 5.0 wt. % (based on the dye carrier composition).

As a rule, the pH of the ready-for-use colorant is about 3 to 11 and preferably 6 to 11, a pH of 6.5 to 8.5 being particularly preferred. The pH of the ready-for-use colorant obtained by mixing the enamine-containing component A1 with the carbonyl-containing component A2 depends on the pH of components A1 and A2 and on the mixing ratio of these two components. If necessary, after mixing components A1 and A2 the pH of the ready-for-use colorant can be adjusted to the desired value by adding an alkalinizing agent or an acid.

Suitable for adjusting the pH of the ready-for-use colorant and of components A1 and A2 are alkalinizing agents such as, for example, alkanolamines, alkylamines, alkali metal hydroxides or ammonium hydroxide, alkali metal carbonates or ammonium carbonate, or acids such as, for example, lactic acid, acetic acid, tartaric acid, phosphoric acid, hydrochloric acid, citric acid, ascorbic acid and boric acid.

The ready-for-use colorant is prepared immediately before use by mixing component A1 containing the compounds of formulas (I) and (Ia) with component A2 containing the carbonyl compound (optionally with addition of an alkalinizing agent or an acid) and is then applied to the fibers. Depending on the depth of shade, this mixture is allowed to act at a temperature from 20 to 50° C., preferably from 30 to 40° C., for 5 to 60 minutes and preferably for 15 to 30 minutes. The fibers are then rinsed with water and optionally washed with a shampoo.

The colorant of the invention permits gentle, uniform and lasting dyeing of the fibers, particularly keratin fibers, for example hair. Surprisingly, the resulting colorations can be removed at any time completely, quickly and gently by use of a reducing agent.

Another object of the present invention is therefore a multicomponent kit for dyeing and later decolorizing fibers, for example wool, silk, cotton or hair and particularly human hair, said kit being characterized in that it contains the dyeing agent (A) of the invention and a decolorizing component (B), said component B containing as the decolorizing agent at least one sulfite, for example ammonium sulfite, alkali metal sulfite or alkaline earth sulfite, and particularly sodium sulfite or ammonium sulfite.

The total amount of sulfites in component B is from about 0.1 to 10 wt. % and preferably from 2 to 5 wt. %.

The agent for decolorizing the fibers dyed with colorant A (in the following referred to as "decolorizer") can be in the form of an aqueous or aqueous-alcoholic solution, gel, cream, emulsion or foam, it being possible to package the decolorizer either in the form of a one-component preparation or in the form of a multicomponent preparation. The decolorizer can be packaged in the form of a powder or, to avoid dusting, in the form of tablets, including effervescent tablets, or as a granulate. Before use, the decolorizer is prepared with cold or warm water, optionally with addition of one or more of the auxiliary agents indicated in the following. It is also possible, however, for these auxiliary agents (if they are in a solid form) to be already contained in the decolorizing powder, decolorizing granulate or effervescent tablets. By wetting the powder with an oil or wax, dusting can be additionally reduced.

The decolorizer can also contain auxiliary agents, for example, a solvent such as water, a lower alcohol, for example ethanol, n-propanol, or isopropanol, a glycol ether or a polyol such as glycerol and, particularly 1,2-propanediol, furthermore a wetting agent or emulsifier from the classes of anionic, cationic, amphoteric or nonionic surface-active agents, such as fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty esters, furthermore thickeners such as higher fatty alcohols, starch or cellulose derivatives, perfumes, hair pretreatment agents, conditioners, hair swelling agents, preservatives, vaselines, paraffin oils and fatty acids as well as hair-care agents, such as cationic resins, lanolin derivatives, cholesterol, pantothenic acid and betaine.

The pH of the decolorizer is from about 3 to 8 and particularly from 4 to 7. If necessary, the desired pH can be obtained by adjustment with a suitable acid, for example an α-hydroxycarboxylic acid such as lactic acid, tartaric acid, citric acid or malic acid, or phosphoric acid, acetic acid, glycolic acid, salicylic acid, glutathione or gluconolactone, or with an alkalinizing agent such as an alkanolamine, alkylamine, alkali metal hydroxide, ammonium hydroxide, alkali metal carbonate, ammonium carbonate or alkali metal phosphate.

Depending on the color to be removed and the temperature (about 20 to 50° C.), the exposure time to the decolorizer is from 5 to 60 minutes and particularly from 15 to 30 minutes. The decolorizing process can be accelerated by the action of heat. At the end of the exposure to the decolorizer, the hair is rinsed with water and optionally washed with a shampoo.

Although component B is well suited for decolorizing hair, particularly human hair, dyed with dye A, component B can in principle also be used for decolorizing other natural or man-made fibers dyed with colorant A, for example cotton, wool, silk, viscose, nylon and cellulose acetate.

The following examples will explain the object of the invention in greater detail without limiting its scope to the examples.

EXAMPLES

Examples 1.1 to 1.12

Synthesis of the Indole Derivatives of Formula (I)/(Ia)

General Method of Synthesis

1a) General Method for Preparing the 3H-Indole Derivatives of Formula (I)/(Ia)

Dissolve the substituted arylhydrazine (1 equivalent) in ethanol at 25° C. Add 1.2 equivalents of the alkyl ketone and heat 3 hours at reflux. Cool to about 60° C. and to the resulting arylhydrazone solution add dropwise concentrated sulfuric acid, then heat for an additional 5 hours at reflux. Cool the re-action solution to 25° C. and concentrate it under reduced pressure to half its original volume. Add distilled water to this reaction solution and make it alkaline by adding four-molar sodium hydroxide solution. Extract the resulting emulsion with diethyl ether. Combine the organic phases, dry over $Na_2SO_4$, filter and concentrate. Purify the resulting oil by bulb-tube distillation.

1b) General Method for the N-Alkylation of the 3H-Indole Derivatives from Step 1a Variant 1

Dissolve the intermediate obtained in 1a) (II equivalent) in chloroform and to the solution add methyl iodide (1.1 to 2.1 equivalents). Stir the resulting solution at 25° C. for 24 hours under an argon atmosphere with exclusion of light. To this solution add tertbutyl methyl ether, collect the yellow precipitate by suction filtration and crystallize it from ethanol.

Variant 2

Stir a suspension of the intermediate obtained in 1a) (1 equivalent) in methyl iodide (5 equivalents) for 4 hours with the aid of ultrasound (120 W). Filter off the solid formed, wash it with tert.butyl methyl ether and crystallize it from ethanol.

Variant 3

Dissolve the intermediate obtained in 1a) (1 equivalent) in methanol, add methyl iodide (2 equivalents) and heat at reflux for 12 hours while keeping the reaction solution protected from light and under an argon atmosphere. Evaporate the reaction solution to dryness under reduced pressure. Wash the residue with ethyl acetate and crystallize it from methanol.

Variant 4

Dissolve the intermediate obtained in 1a) (1 equivalent) in 1,2-dichloroethane, add trimethyloxonium tetrafluoroborate (1.2 equivalents) and heat at reflux for 6 hours. Precipitate the product by cooling the reaction mixture to 4° C. or by adding ethyl acetate. Filter off the resulting solid, wash it with a small amount of ethyl acetate and crystallize it from methanol.

1c) General Method for the Demethylation of the Aryl Methyl Ether

Dissolve the aryl methyl ether in acetic acid and add 48% hydrobromic acid solution. Heat the reaction mixture at reflux for 8 hours, then allow it to agitate overnight at room temperature. Neutralize the reaction solution with 20% sodium hydroxide solution, render it alkaline with saturated sodium hydrogen carbonate solution (pH=8.0) and extract with ethyl acetate. Combine the organic phases, wash with water and saturated sodium chloride solution, dry over MgSO$_4$, filter and evaporate to dryness. Crystallize the resulting solid from ethyl acetate.

1d) General Method for the Nitration of the Compounds of Formula (I) or (Ia)

Add the compound of formula (I) or (Ia) portionwise to ice-cooled concentrated sulfuric acid without exceeding a reaction temperature of 10° C. To the resulting solution add dropwise the nitrating acid (100% HNO$_3$ dissolved in 95% H$_2$SO$_4$) while keeping the reaction temperature also below 10° C. Allow the reaction mixture to agitate 3 hours at 5° C., then pour it onto ice and render the aqueous phase alkaline with sodium hydroxide solution. Wash the resulting solid with water and then dissolve it in tert.butyl methyl ether. Wash the organic phase with water, dry it over Na$_2$SO$_4$, filter and evaporate to dryness. Crystallize the crude product from hexane/methylene chloride or dissolve it in hot acetonitrile and a small amount of 3-molar hydrochloric acid (in ethanol) and precipitate the product with water.

1e) General Method for the Reduction of the Nitro Compounds to the Corresponding Arylamines Followed by N-Acetylation Reduction of the Arylic Nitro Group Dissolve the nitro compound prepared under 1d) in 32% aqueous hydrochloric acid and to the solution add SnCl$_2$.2H$_2$O. Heat the reaction mixture at reflux for 1 to 3 hours, then cool to 25° C. Pour the reaction solution onto ice, render the reaction solution alkaline with 4-molar sodium hydroxide solution and extract it with tert.butyl methyl ether. Dry the combined organic phases over Na$_2$SO$_4$, filter, acidify with a 3-molar hydrochloric acid solution (in ethanol) and evaporate to dryness under reduced pressure. Dissolve the residue in a small amount of 3-molar hydrochloric acid (in ethanol) and add the solution to cold tert.butyl methyl ether. Isolate the precipitated product by filtration under nitrogen.

N-Acetylation

Dissolve the aforesaid product in acetic acid and add acetic anhydride to the solution. Allow the reaction mixture to agitate vigorously at 25° C. for 1 to 3 hours, then add it to tert.butyl methyl ether. Collect the resulting precipitate by suction filtration, wash it with ether and dry under vacuum.

Example 1.1

Synthesis of 1,2,3,3,5-Pentamethyl-3H-Indolium Iodide

This compound was prepared by the general synthesis method 1 a) by adding 3.0 mL of 97% sulfuric acid to a solution of 3.27 g of p-tolylhydrazine and 2.87 g of isopropyl methyl ketone in 110 mL of ethanol. The resulting oil was purified by bulb-tube vacuum distillation (0.02–0.07 mbar; 100–105° C.).

Yield (intermediate): 3.18 g of 2,3,3,5-tetramethyl-3H-indole 168% of the theoretical). 1.0 g of the intermediate thus obtained was alkylated with 4.18 g of methyl iodide according to variant 2 under 1b).

Yield: 1.11 g of 1,2,3,3,5-pentamethyl-3H-indolium iodide (61% of the theoretical).

Melting point: 224–227° C.

$^1$H-NMR (CD$_3$OD): δ=1.59 ppm (s, 6H); 2.50 ppm (s, 3H); 4.03 ppm (s, 3H); 4.83 ppm (s, 3H) (s, 3H); 7.45 ppm (dd, $^3$J=8 Hz, $^4$J=not resolved, 1H); 7.59 ppm (d, $^4$J=not resolved, 1H); 7.70 (d, $^3$J=8 Hz, 1H).

FAB$^1$ mass spectrum: M$^+$=188.30 (100% rel intensity)

FAB=fast atom bombardment—Translator

Elemental analysis: C$_{13}$H$_{18}$NI (315.19)

|  | % C | % H | % N |
|---|---|---|---|
| Calcd.: | 49.54 | 5.76 | 4.74 |
| Found: | 49.80 | 5.77 | 4.30 |

Example 1.2

Synthesis of 1,2,3,3,7-Pentamethyl-3H-Indolium Tetrafluoroborate

This compound was prepared by the general synthesis method 1a) by adding 3.1 mL of 97% sulfuric acid to a solution of 3.39 g of p-tolylhydrazine and 3.0 g of isopropyl methyl ketone in 120 mL of ethanol. The resulting oil was purified by bulb-tube vacuum distillation (0.02–0.07 mbar; 100–105° C.).

Yield (intermediate): 3.0 g of 2,3,3,7-tetramethyl-3H-indole (62% of the theoretical) 0.50 g of the intermediate thus obtained was alkylated with 0.51 g of trimethyloxonium tetrafluoroborate and 1 mL of 1,2-dichloroethane according to variant 4 under 1b).

Yield; 0.43 g of 1,2,3,3,7-pentamethyl-3H-indolium tetrafluoroborate (54% of the theoretical) $^1$H-NMR D$_6$-DMSO): δ=1.50 ppm (s, 6H); 2.74 ppm (s, 3H); 2.75 ppm (s, 3H); 4.11 ppm (s, 3H); 7.35 ppm (dd, $^3$J=7.5 Hz, $^4$J=not resolved, 1H); 7.46 ppm (dd, $^3$J=7.5 Hz, 1H); 7.60 ppm (dd, $^3$J=7.5 Hz, $^4$J=not resolved, 1H).

FAB mass spectrum: M$^+$=188.3 (100% rel. intensity)

Elemental analysis: C$_{13}$H$_{18}$NBF$_4$ (275.10)

|  | % C | % H | % N | % F |
|---|---|---|---|---|
| Calcd.: | 56.76 | 6.60 | 5.09 | 27.62 |
| Found | 56.52 | 6.48 | 5.21 | 27.57 |

Example 1.3

Synthesis of 1,2,3,3,6,7-Hexamethyl-3H-Indolium Tetrafluoroborate

This compound was prepared by the general synthesis method 1a) by adding 3.1 mL of 97% sulfuric acid to a solution of 3.76 g of dimethylphenylhydrazine and 2.97 g of isopropyl methyl ketone in 120 mL of ethanol. The resulting oil was purified by bulb-tube vacuum distillation (0.02–0.07 mbar; 100–105° C.).

Yield (intermediate): 1.90 g of 2,3,3,6,7-pentamethyl-3H-indole (37% of the theoretical).

1.0 g of the intermediate thus obtained was alkylated with 0.95 g of trimethyloxonium tetrafluoroborate and 4 mL of 1,2-dichloroethane according to variant 4 under 1b).

Yield 0.49 g of 1,2,3,3,6,7-hexamethyl-3H-indolium tetrafluoroborate (32% of the theoretical).

$^1$H(D$_6$-DMSO): δ=1.45 ppm (s, 6H); 2.37 ppm (s, 3H); 2.61 ppm (s, 3H); 2.72 ppm (s, 3H); 4.11 pm (s, 3H); 7.40 ppm (d, $^3$J=8 Hz, 1H); 7.49 ppm (d, $^3$J=8 Hz, 1H).

FAB mass spectrum: M$^+$=202.3 (100% rel intensity)

Elemental analysis: C$_{14}$H$_{20}$NBF$_4$ (289.121)

|  | % C | % H | % N | % F |
|---|---|---|---|---|
| Calcd.: | 58.16 | 6.97 | 4.84 | 26.28 |
| Found | 57.86 | 6.88 | 4.78 | 26.15 |

Example 1.4

Synthesis of 1,2,3,3,5,7-Hexamethyl-3H-Indolium Tetrafluoroborate

This compound was prepared by the general synthesis method 1a) by adding 3.2 mL of 97% sulfuric acid to a solution of 4.57 g of dimethylphenylhydrazine and 3.08 g of isopropyl methyl ketone in 80 mL of ethanol. The resulting oil was purified by bulb-tube vacuum distillation (0.02–0.07 mbar; 100–105° C./).

Yield (intermediate): 2.67 g of 2,3,3,5,7-pentamethyl-3H-indole (50% of the theoretical).

1.0 g of the intermediate thus obtained was alkylated with 0.95 g of trimethyloxonium tetrafluoroborate and 4 mL of 1,2-dichloroethane according to variant 4 under 1b).

Yield 0.79 g of 1,2,3,3,5,7-hexamethyl-3H-indolium tetrafluoroborate (51% of the theoretical).

$^1$H-NMR (D$_6$-DMSO): δ=1.45 ppm (s, 6H); 2.36 ppm (s, 3H); 2.69 ppm (s, 3H); 2.70 ppm (s, 3H); 4.07 ppm (s, 3H); 7.18 ppm (s, 1H); 7.44 ppm (s, 1H).

FAB mass spectrum: M$^+$=202.3 (100% rel intensity)

Elemental analysis: C$_{14}$H$_{20}$NBF$_4$ (289.12)

|  | % C | % H | % N | % F |
|---|---|---|---|---|
| Calcd.: | 58.16 | 6.97 | 4.84 | 26.28 |
| Found | 57.94 | 6.86 | 4.81 | 26.32 |

Example 1.5

Synthesis of 1,2,3,3,4,7-Hexamethyl-3H-Indolium Tetrafluoroborate

This compound was prepared by the general synthesis method 1a) by adding 3.1 mL of 97% sulfuric acid to a solution of 3.70 g of dimethylphenylhydrazine and 2.93 g of isopropyl methyl ketone in 80 mL of ethanol. The resulting oil was purified by bulb-tube vacuum distillation (0.02–0.07 mbar; 100–105° C.).

Yield (intermediate): 3.58 g of 2,3,3,4,7-pentamethyl-3H-indole (70% of the theoretical).

1.0 g of the intermediate thus obtained was alkylated with 0.95 g of trimethyloxonium tetrafluoroborate and 4 mL of 1,2-dichloroethane according to variant 4 under 1b).

Yield; 0.83 g of 1,2,3,3,4,7-hexamethyl-3H-indolium tetrafluoroborate (53% of the theoretical).

$^1$H-NMR D$_6$-DMSO): δ=1.53 ppm (s, 6H); 2.47 ppm (s, 3H); 2.70 ppm (s, 3H); 2.72 ppm (s, 3H); 4.07 ppm (s, 3H); 7.23 ppm (d, $^3$J=8 Hz, 1H); 7.27 ppm (d, $^3$J=8 Hz, 1H).

FAB mass spectrum: M$^+$=202.3 (100% rel intensity)

Elemental analysis: C$_{14}$H$_{20}$NBF$_4$ (289.12)

|  | % C | % H | % N | % F |
|---|---|---|---|---|
| Calcd.: | 58.16 | 6.97 | 4.84 | 26.28 |
| Found | 58.10 | 6.86 | 4.80 | 26.11 |

Example 1.6

Synthesis of 5-Methoxy-1,2,3,3-Tetramethyl-3H-Indolium Iodide

This compound was prepared by the general synthesis method 1a) by adding 8.0 g of 4-methoxyphenylhydrazine and 6.23 g of isopropyl methyl ketone to 120 mL of ethanol and 11.3 g of 97% sulfuric acid. The resulting oil was purified by bulb-tube vacuum distillation (0.02–0.07 mbar; 100–105° C.).

Yield (intermediate): 6.34 g of 5-methoxy-2,3,3,-trimethyl-3H-indole (58% of the theoretical).

1.0 g of the intermediate thus obtained was alkylated with 1.59 g of methyl iodide and 7.2 mL of chloroform according to variant 1 under 1b).

Yield: 1.11 g of 1,2,3,3,5-pentamethyl-3H-indolium iodide (58% of the theoretical).

$^1$H-NMR (CD$_3$OD): δ=1.59 ppm (s, 6H); 3.91 ppm (s, 3H); 4.02 ppm (s, 3H); 4.85 ppm (s, 3H); 7.15 ppm (dd, $^3$J=9 Hz, $^4$J=2 Hz, 1H); 7.35 ppm (d, $^4$J=2 Hz, 1H); 7.73 ppm (d, $^3$J=9 Hz, 1H).

FAB mass spectrum: M$^+$=204.0 (100% rel. intensity), 188 (44% rel. intensity)

Elemental analysis: C$_{13}$H$_{18}$NOI (331.20)

|  | % C | % H | % N | % O |
|---|---|---|---|---|
| Calcd.: | 47.15 | 5.48 | 4.23 | 4.83 |
| Found | 47.30 | 6.10 | 4.30 | 4.90 |

Example 1.7

Synthesis of 5-Fluoro-1,2,3,3-Tetramethyl-3H-Indolium Iodide

This compound was prepared by the general synthesis method 1 a) by adding 3.0 g of 4-fluorophenyl-hydrazine and 2.48 g of isopropyl methyl ketone to 65 mL of ethanol and 2.6 mL of 97% sulfuric acid. The resulting solid was melted and purified by bulb-tube vacuum distillation (0.02–0.07 mbar; 100–105° C.).

Yield (intermediate): 3.21 g of 5-fluoro-2,3,3-trimethyl-3H-indole (76% of the theoretical).

1.0 g of the intermediate thus obtained was alkylated with 0.91 g of methyl iodide and 3 mL of chloroform according to variant 1 under 1b).

Yield: 0.70 g (39% of the theoretical).

$^1$H-NMR (CD$_3$OD): δ=1.62 ppm (s, 6H); 4.06 ppm (s, 3H); 4.85 ppm (s, 3H); 7.38–7.42 ppm (m, 1H); 7.61–7.63 ppm (m, 1H); 7.86–7.89 ppm (m, 1H).

FAB mass spectrum: M$^+$=192.20 (100% rel. intensity)

Elemental analysis: C$_{12}$H$_{15}$NFI (319.16)

|  | % C | % H | % N | % F |
|---|---|---|---|---|
| Calcd.: | 45.16 | 4.74 | 4.39 | 5.95 |
| Found | 44.70 | 4.90 | 4.30 | 6.00 |

Example 1.8

Synthesis of 5-Isopropyl-1,2,3,3-Tetramethyl-3H-Indolium Iodide

This compound was prepared by the general synthesis method 1a) by adding 3.71 g of 4-isopropyl-phenylhydrazine and 2.66 g of isopropyl methyl ketone to 90 mL of ethanol and 2.9 mL of 97% sulfuric acid. The resulting oil was purified by bulb-tube vacuum distillation (0.02–0.07 mbar; 100–105° C).

Yield (intermediate): 4.11 g of 5-isopropyl-2,3,3-trimethyl-3H-indole (83% of the theoretical).

1.0 g of the intermediate thus obtained was alkylated with 0.81 g of methyl iodide and 3 mL of chloroform according to variant 1 under 1b).

Yield: 0.63 g of 5-isopropyl-1,2,3,3-tetramethyl-3H-indolium iodide (37% of the theoretical).

$^1$H-NMR (CD$_3$OD): δ=1.31 ppm (d, $^3$J=7 Hz, 6H); 1.60 ppm (s, 6H); 3.06–3.12 (m, 1H); 4.04 ppm (s, 3H); 4.84 ppm (s, 3H); 7.52 ppm (dd, $^3$J=9 Hz, $^4$J 2 Hz, 1H); 7.66 ppm (d, $^4$J=2 Hz, 1H); 7.73 ppm (d, $^3$J=8 Hz, 1H).

FAB mass spectrum: M$^+$216.3 (100% rel. intensity)

Elemental analysis: C$_{16}$H$_{22}$NI (343.31)

|  | % C | % H | % N |
|---|---|---|---|
| Calcd.: | 52.48 | 6.46 | 4.08 |
| Found | 52.90 | 6.80 | 3.82 |

Example 1.9

Synthesis of 5-Hydroxy-1,2,3,3-Tetramethyl-3H-Indolium Iodide

This compound was prepared by the general synthesis method 1c) from 4.0 g of 5-methoxy-2,3,3-trimethyl-3H-indole, 16 mL of acetic acid and 16 mL of 48% hydrobromic acid solution.

Yield (intermediate): 2.45 g of 5-hydroxy-2,3,3-trimethyl-3H-indole (66% of the theoretical).

1.0 g of the intermediate thus obtained was alkylated with 1.66 g of methyl iodide and 10 mL of methanol according to variant 3 under 1b).

Yield: 1.36 g of 5-hydroxy-1,2,3,3-tetramethyl-3H-indolium iodide (75% of the theoretical).

Melting point: 245–247° C.

$^1$H-NMR (D$_6$-DMSO): δ=1.46 ppm (s, 6H); 2.66 ppm (s, 3H); 3.89 ppm (s, 3H); 6.93 ppm (dd, $^3$J=9 Hz, $^4$J=2 Hz, 1H); 7.11 ppm (d, $^4$J=2 Hz, 1H); 7.67 ppm (d, $^3$J=9 Hz, 1H); 10.22 ppm (s, exchanges with D$_2$O, 1H).

FAB mass spectrum: M$^+$=190.10 (100% rel. intensity)

Elemental analysis: C$_{12}$H$_{16}$NOI (317.17)

|  | % C | % H | % N | % O |
|---|---|---|---|---|
| Calcd.: | 45.44 | 5.08 | 4.42 | 5.04 |
| Found | 45.50 | 5.60 | 4.40 | 5.60 |

Example 1.10

Synthesis of 5-Nitro-1,3,3-Trimethyl-2-Methyleneindoline

This compound was prepared by the general synthesis method 1d) from a solution of 20 g of 1,3,3-trimethyl-2-methyleneindoline in 50 mL of 97% sulfuric acid and 23.5 mL of nitrating acid (a mixture of 3.5 mL of fuming 99% nitric acid and 20 mL of 97% sulfuric acid). The crude product was crystallized from hexane/methylene chloride.

Yield: 8.8 g of 5-nitro-1,3,3-trimethyl-2-methyleneindoline (35% of the theoretical).

Melting point: 89–91° C.

$^1$H-NMR (CDCl$_3$): δ=1.35 ppm (s, 6H); 3.11 ppm (s,3H); 4.09 ppm (d, $^2$J=3 Hz, 1H); 4.11 ppm (d, $^2$J=2.5 Hz, 1H); 6.51 ppm (d, $^3$J=9 Hz, 1H); 7.91 ppm (d, $^4$J=2.5 Hz, 1H); 8.11 ppm (dd, $^2$J=9 Hz, $^4$J=2.5 Hz, 1H);

EI mass spectrum: 218 (85, M$^+$); 203 (100); 188 (6); 171 (16); 157 (91); 145 (32); 1.45 (32); 1.28 (24); 115 (44); 103 (10); 89 (15); 77 (14); 63 (12).

Example 1.11

Synthesis of 5-Methoxy-6-Nitro-1,2,3,3-Tetramethyl-3H-Indolium Chloride

This compound was prepared by the general synthesis method 1d) from a solution of 0.50 g of 5-methoxy-1,2,3,3-tetramethyl-3H-indolium iodide in 5 mL of 97% sulfuric acid and using 0.5 ml of nitrating acid (mixture consisting of 1.5 mL of fuming 99% nitric acid and 10 mL of 97% sulfuric acid). The crude product was dissolved in about 2 mL of hot acetonitrile with the aid of 3 M hydrochloric acid in ethanol (about 0.5 mL). Addition of water caused the pure product to precipitate.

Yield: 0.22 g of 5-methoxy-6-nitro-1,2,3,3-tetramethyl-3H-indolium chloride (45% of the theoretical).

$^1$H-NMR (D$_6$-DMSO): δ=1.58 ppm (s, 6H); 2.78 ppm (s, 3H); 3.98 ppm (s, 3H); 4.05 ppm (s, 3H); 8.05 ppm (s, 1H); 8.60 ppm (s, 1H)

$^{13}$C-NMR (D$_6$DMSO) δ=14.4 ppm (q); 21.5 ppm (q); 35.2 ppm (q); 54.7 ppm (s); 57.9 ppm (q); 110.2 ppm (d); 112.3 ppm (d); 134.5 ppm (s); 139.0 ppm (s); 147.4 ppm (s); 153.1 ppm (s); 196.2 ppm (s).

FAB mass spectrum: M$^+$249.2 (100% rel. intensity)

Elemental analysis: C$_{13}$H$_{17}$N$_2$O$_3$Cl (284.74)

|  | % C | % H | % N | % O |
|---|---|---|---|---|
| Calcd.: | 54.84 | 6.02 | 9.84 | 16.86 |
| Found | 54.30 | 5.80 | 9.70 | 17.40 |

Example 1.12

Synthesis of 5-N-Acetylamino-1,2,3,3-Tetramethyl-3H-Indolium Acetate

This compound was prepared by the general synthesis method 1e) and using for the reaction 1.3 g of 5-nitro-1,3,3-trimethyl-2-methyleneindoline, 39 mL of 32% hydrochloric acid and 8.10 g of SnCl$_2$. 2 H$_2$O. The N-acetylation reaction was carried out with 1.48 g of 5-amino-1,2,3,3- tetramethyl-3H-indolium chloride, 37 mL of acetic acid and 37 mL of acetic anhydride.

Yield: 1.41 g of 5-N-acetylamino-1,2,3,3-tetramethyl-3H-indolium acetate (82% of the theoretical).

$^1$H-NMR (D$_6$-DMSO): δ=1.48 ppm (s, 6H); 1.90 ppm (s, 3H from AcO$^-$); 2.09 ppm (s, 3H); 2.71 ppm (s, 3H); 3.93 ppm (s, 3H); 7.74 ppm (dd, $^3$J=9 Hz, $^4$J=2 Hz, 1H); 7.83 ppm (d, $^3$J=9 Hz, 1H); 8.08 ppm (d, $^4$J=2 Hz, 1H); 10.73 ppm (s, 1H).

EI mass spectrum: 230 (67, M$^+$); 215 (100); 199 (5); 187 (10); 173 (25); 145 (35); 130 (10); 115 (6); 103 (5); 77 (8).

Example 1.13

Synthesis of 1,2-Dimethyl-5-Methoxy-3-(Spirocyclohexyl)-3H-Indolium Tetrafluoroborate This compound was prepared by the general synthesis method 1a) from 3.0 g of 4-methoxyphenyl-hydrazine, 3.42 g of cyclohexyl methyl ketone in 50 mL of ethanol and 4.43 g of 97% sulfuric acid. The resulting oil was purified by chromatography (silica gel; hexane:EtOAc=6:4). This gave 1.46 g of 5-methoxy-2-methyl-3-(spirocyclohexyl)-3H-indole (29% of the theoretical).

1.11 of the intermediate thus obtained was alkylated with 3.10 g of trimethyloxonium tetrafluoroborate (4.3 equivalents) and 20 mL of 1,2-dichloroethane according to synthesis method 1b) (variant 4).

Yield: 1.26 g of 1,2-dimethyl-5-methoxy-3-(spirocyclohexyl)-3H-indolium tetrafluoroborate (79% of the theoretical).

$^1$H-NMR (D$_6$DMSO): δ=1.33–1.60 ppm (m, 3H); 1.70–2.10 ppm (m, 7H); 2.71 ppm (s, 3H); 3.88 ppm (s, 3H); 3.92 ppm (s, 3H); 7.21 ppm (dd, $^3$J=9 Hz, $^4$J=2.0 Hz, 1H); 7.51 ppm (d, $^4$J=2.0 Hz, 1H); 7.86 ppm (d, $^3$J=9.0 Hz, 1H).

FAB mass spectrum: M$^+$=244.2 (100% rel. intensity)

| Elemental analysis: C$_{16}$H$_{22}$NOBF$_4$ (331.16) | | | | | |
|---|---|---|---|---|---|
| | % C | % H | % N | % F | % O |
| Calcd.: | 58.03 | 6.70 | 4.23 | 22.95 | 4.83 |
| Found | 57.70 | 6.80 | 4.20 | 23.00 | 4.80 |

Examples 2.1 to 5.5

Hair Coloring Solution

| Indole-Containing Component A1 | |
|---|---|
| Indole derivative of formula (I)/(Ia) | Quantities shown in Tables 1–4 |
| Lauryl ether sulfate (28% aqueous solution) | 1 g |
| Ethanol | 2 g |
| Water, demineralized | to 10 g |

The pH of the solution was adjusted to the value indicated in Tables 1 to 4 with 20% aqueous monoethanolamine solution.

| Aldehyde-Containing Component A2 | |
|---|---|
| Aldehyde compound | Quantities shown in Tables 1–4 |
| Lauryl ether sulfate (28% aqueous solution) | 1 g |
| Ethanol | 2 g |
| Water, demineralized | to 10 g |

The pH of component A2 was between 4 and 5.

1 g of component A1 was mixed with 1 g of component A2. The resulting pH, (pH of the mixture of components A1+A2) is given in Tables 1 to 4.

The resulting ready-for-use hair colorant was applied to bleached hair and uniformly distributed with a brush. After an exposure time of 30 min at 40° C., the hair was washed with a shampoo, rinsed with luke-warm water and then dried.

The hair can be completely decolorized at any point in time (for example after several days or weeks) within 20 min at 40° C. with an acidic (pH=5) 5% sodium sulfite solution.

The results of the coloring and decolorizing are summarized in the following Tables 1 to 4.

TABLE 1

| | | | Coloring Results | | | |
|---|---|---|---|---|---|---|
| No. | A1) Indole-containing component, pH 8.8 A2) Aldehyde-containing component | Shade After Coloring | | Color-Measuring Values | | |
| | | | | L | a | b |
| 2.1 | A1) 1,2,3,3,5-pentamethyl-3H-indolium iodide, 0.30 g, A2) 3,5-dimethoxy-4-hydroxybenzaldehyde, 0.17 g, pH$_m$: 8.1 | purple | untreated hair after dyeing | +83.30 +39.01 | −0.48 +36.77 | +10.40 +0.13 |

TABLE 1-continued

Coloring Results

| No. | A1) Indole-containing component, pH 8.8<br>A2) Aldehyde-containing component | Shade After Coloring | | Color-Measuring Values | | |
|---|---|---|---|---|---|---|
| | | | | L | a | b |
| 2.2 | A1) 1,2,3,3,5-pentamethyl-3H-indolium iodide, 0.30 g<br>A2) 4-hydroxy-3-methoxy-benzaldehyde, 0.15 g,<br>pH$_m$: 7.9 | intense orange | untreated hair<br>after dyeing | +83.30<br>+51.07 | −0.48<br>43.03 | +10.40<br>+23.06 |
| 2.3 | A1) 1,2,3,3,5-pentamethyl-3H-indolium iodide, 0.30 g<br>A2) 3-hydroxy-4-methoxy-benzaldehyde, 0.15 g<br>pH$_m$: 8.7 | intense yellow | untreated hair<br>after dyeing | +83.30<br>+75.13 | −0.48<br>+12.17 | +10.40<br>+73.24 |
| 2.4 | A1) 1,2,3,3,5-pentamethyl-3H-indolium iodide, 0.30 g<br>A2 3,4,5-trihydroxy-benzaldehyde, 0.16 g,<br>pH$_m$: 7.8 | intense wine-red | untreated hair<br>after dyeing | +83.30<br>+30.54 | −0.48<br>+28.38 | +10.40<br>+1.58 |
| 2.5 | A1) 1,2,3,3,5-pentamethyl-indolium iodide, 0.30 g<br>A2) 4-(dimethylamino)-benzaldehyde, 0.14 g<br>pH$_m$: 8.8 | intense pink | untreated hair<br>after dyeing | +83.30<br>+52.58 | −0.48<br>+61.46 | +10.40<br>+4.29 |

TABLE 2

Coloring Results

| No. | A1) Indole-containing component, pH 8.2<br>A2) Aldehyde-containing component | Shade After Coloring/Decolorizing | | Color-Measuring Values | | |
|---|---|---|---|---|---|---|
| | | | | L | a | b |
| 3.1 | A1) 5-isopropyl-1,2,3,3-tetramethyl-3H-indolium iodide, 0.33 g<br>A2) 3,5-dimethoxy-4-hydroxy-benzaldehyde, 0.17 g<br>pH$_m$: 7.7 | purple<br>after decolorizing white | untreated hair<br>after dyeing | +83.30<br>+36.29 | −0.48<br>+40.00 | +10.40<br>−1.35 |
| 3.2 | A1) 5-isopropyi-1,2,3,3-tetramethyl-3H-indolium iodide, 0.33 g<br>A2) 4-hydroxy-3-methoxy benzaldehyde, 0.15 g<br>pH$_m$: 7.7 | intense orange<br>after decolorizing white | untreated hair<br>after dyeing | +83.30<br>+48.10 | −0.48<br>+49.18 | +10.40<br>+25.14 |
| 3.3 | A1) 5-isopropyl-1,2,3,3-tetramethyl-3H-indolium iodide, 0.33 g<br>A2) 3-hydroxy-4-methoxy-benzaldehyde, 0.15 g<br>pH$_m$: 8.3 | intense yellow<br>after decolorizing white | untreated hair<br>after dyeing | +83.30<br>+75.70 | −0.48<br>+11.98 | +10.40<br>+64.39 |
| 3.4 | A1) 5-isopropyl-1,2,3,3-tetramethyl-3H-indolium iodide, 0.33 g<br>A2) 3,4,5-trihydroxybenzaldehyde, 0.16 g<br>pH$_m$: 7.6 | intense eggplant<br>after decolorizing white | untreated hair<br>after dyeing | +83.30<br>+40.79 | −0.48<br>+15.34 | +10.40<br>+0.69 |
| 3.5 | A1) 5-isopropyl-1,2,3,3-tetramethyl-3H-indolium iodide, 0.33 g<br>A2) 4-(dimethylamino)benzaldehyde 0.14 g<br>pH$_m$: 8.4 | intense pink<br>after decolorizing white | untreated hair<br>after dyeing | +83.30<br>+57.30 | −0.48<br>+56.83 | +10.40<br>+1.75 |

TABLE 3

Coloring Results

| No. | A1) Indole-containing component, pH 8.5<br>A2) Aldehyde-containing component | Shade After Coloring/ Decolorizing | | Color-Measuring Values | | |
|---|---|---|---|---|---|---|
| | | | | L | a | b |
| 4.1 | A1) 5-fluoro-1,2,3,3-tetramethyl-3H-indolium iodide, 0.30 g<br>A2) 3,5-dimethoxy-4-hydroxy-benzaldehyde, 0.17 g<br>$pH_m$: 7.8 | eggplant<br><br>after decolorizing | untreated hair<br>after dyeing<br>white | +83.30<br>+35.91 | −0.48<br>+44.47 | +10.40<br>−11.23 |
| 4.2 | A1) 5-fluoro-1,2,3,3-tetramethyl-3H-indolium iodide, 0.30 g<br>A2) 4-hydroxy-3-methoxybenz-aldehyde, 0.15 g<br>$pH_m$: 7.9 | red<br><br>after decolorizing | untreated hair<br>after dyeing<br>white | +83.30<br>+40.79 | −0.48<br>+59.23 | +10.40<br>+20.40 |
| 4.3 | A1) 5-fluoro-1,2,3,3-tetramethyl-3H-indolium iodide, 0.30 g<br>A2) 3-hydroxy-4-methoxy-benzaldehyde, 0.15 g<br>$pH_m$: 8.5 | intense yellow<br>after decolorizing | untreated hair<br>after dyeing<br>white | +83.30<br>+72.32 | −0.48<br>+17.57 | +10.40<br>+77.71 |
| 4.4 | A1) 5-fluoro-1,2,3,3-tetramethyl-3H-indolium iodide, 0.30 g<br>A2) 3,4,5-trihydroxybenz-aldehyde, 0.16 g<br>$pH_m$: 7.8 | eggplant<br><br>after decolorizing | untreated hair<br>after dyeing<br>white | +83.30<br>+29.44 | −0.48<br>+27.82 | +10.40<br>−10.86 |
| 4.5 | A1) 5-fluoro-1,2,3,3-tetramethyl-3H-indolium iodide, 0.30 g<br>A2) 4-(dimethylamino)benz-aldehyde, 0.14 g<br>$pH_m$: 8.5 | intense pink<br>after decolorizing | untreated hair<br>after dyeing<br>light-pink | +83.30<br>+58.58 | −0.48<br>+55.54 | +10.40<br>+1.32 |

TABLE 4

Coloring Results

| No. | A1) Indole-containing component, pH 9.4<br>A2) Aldehyde-containing component | Shade After Coloring | | Color-Measuring Values | | |
|---|---|---|---|---|---|---|
| | | | | L | a | b |
| 5.1 | A1) 5-methoxy-1,2,3,3-tetramethyl-3H-indolium iodide, 0.32 g<br>A2) 3,5-dimethoxy-4-hydroxy-benzaldehyde, 0.17 g<br>$pH_m$: 8.3 | wine-red | untreated hair<br>after dyeing | +83.30<br>+23.77 | −0.48<br>+42.40 | +10.40<br>+7.96 |
| 5.2 | A1) 5-methoxy-1,2,3,3-tetramethyl-3H-indolium iodide, 0.32 g<br>A2) 4-hydroxy-3-methoxybenz-aldehyde, 0.15 g<br>$pH_m$: 8.2 | red | untreated hair<br>after dyeing | +83.30<br>+36.46 | −0.48<br>+55.82 | +10.40<br>+31.27 |
| 5.3 | A1) 5-methoxy-1,2,3,3-tetramethyl-3H-indolium iodide, 0.32 g<br>A2) 3-hydroxy-4-methoxy-benzaldehyde, 0.15 g<br>$pH_m$: 8.6 | orange | untreated hair<br>after dyeing | +83.30<br>+62.18 | −0.48<br>+35.08 | +10.40<br>+76.67 |
| 5.4 | A1) 5-methoxy-1,2,3,3-tetramethyl-3H-indolium iodide, 0.32 g<br>A2) 3,4,5-trihydroxybenz-aldehyde, 0.16 g<br>$pH_m$: 7.9 | intense wine-red | untreated hair<br>after dyeing | +83.30<br>+20.57 | −0.48<br>+31.59 | +10.40<br>+6.62 |
| 5.5 | A1) 5-methoxy-1,2,3,3-tetramethyl-3H-indolium iodide, 0.32 g<br>A2) 4-(dimethylamino)-benzaldehyde, 0.14 g<br>$pH_m$: 8.7 | intense pink | untreated hair<br>after dyeing | +83.30<br>+38.52 | −0.48<br>+64.34 | +10.40<br>+4.33 |

Coloring Examples 6.1 to 12.5

Hair Colorants in Cream Form

Component A1 with Indole Derivative

| Indole derivative of formula (I)/(Ia) | Quantities shown in Tables 5–11 |
|---|---|
| Cetylstearyl alcohol | 12 g |
| Lauryl ether sulfate, 28% aqueous solution | 10 g |
| Ethanol | 23 g |
| Water, demineralized | to 100 g |

The cetylstearyl alcohol was melted at 80° C. The lauryl ether sulfate and 95% of the water were heated to 80° C., added to the molten cetylstearyl alcohol and stirred until a cream formed. Compound (I)/(Ia) mixed with the ethanol and the remainder of the water were added at room temperature. The pH of the cream was adjusted to the value given in Tables 5 to 10 with 20% aqueous monoethanolamine solution.

Aldehyde Component A2

| Aldehyde compound | Quantities shown in Tables 5–11 |
|---|---|
| Cetylstearyl alcohol | 12 g |
| Lauryl ether sulfate, 28% aqueous solution | 10 g |
| Ethanol | 23 g |
| Water, demineralized | to 100 g |

The cetylstearyl alcohol was melted at 80° C. The lauryl ether sulfate and 95% of the water were heated to 80° C., added to the molten cetylstearyl alcohol and stirred until a cream formed. The aldehyde mixed with the ethanol and the remainder of the water were added at room temperature. The pH of component A2 was between 4 and 5.

Components A1 and A2 were mixed in a 1:1 ratio. The measured pH of the mixture is indicated in Tables 5 to 11 as $pH_m$. The ready-for-use hair colorant obtained in this manner was applied to bleached hair and uniformly distributed with a brush. After an exposure time of 30 min at 40° C., the hair was washed with a shampoo, rinsed with luke-warm water and then dried.

The hair can be completely decolorized at any point in time (for example after several days or weeks) within 20 min at 40° C. with an acidic (pH=5) 5% sodium sulfite solution.

The results of the coloring and decolorizing are summarized in the following Tables 5 to 11.

TABLE 5

Coloring Results

| No. | A1) Indole-containing component, pH 7.6<br>A2) Aldehyde-containing component | Shade After Coloring/Decolorizing | | Color-Measuring Values | | |
|---|---|---|---|---|---|---|
| | | | | L | a | b |
| 6.1 | A1) 1,2,3,3,5-pentamethyl-3H-indolium iodide, 3.62 g<br>A2) 3,5-dimethoxy-4-hydroxy-benzaldehyde, 2.09 g<br>$pH_m$: 7.6 | purple<br>after decolorizing | untreated hair<br>after dyeing<br>white | +83.30<br>+21.23 | −0.48<br>+42.37 | +10.40<br>+2.40 |
| 6.2 | A1) 1,2,3,3,5-pentamethyl-3H-indolium iodide, 3.62 g<br>A2) 4-hydroxy-3-methoxy-benzaldehyde, 1.75 g<br>$pH_m$: 7.4 | red<br>after decolorizing | untreated hair<br>after dyeing<br>white | +83.30<br>+31.41 | −0.48<br>+57.08 | +10.40<br>+22.71 |
| 6.3 | A1) 1,2,3,3,5-pentamethyl-3H-indolium iodide, 3.62 g<br>A2) 3-hydroxy-4-methoxy-benzaldehyde, 1.75 g<br>$pH_m$: 8.1 | intense yellow<br>after decolorizing | untreated hair<br>after dyeing<br>white | +83.30<br>+61.71 | −0.48<br>+31.44 | +10.40<br>+73.16 |
| 6.4 | A1) 1,2,3,3,5-pentamethyl-3H-indolium iodide, 3.62 g<br>A2) 3,4,5-trihydroxy-benzaldehyde, 1.98 g<br>$pH_m$: 7.6 | intense wine-red<br>after decolorizing | untreated hair<br>after dyeing<br>white | +83.30<br>+18.17 | −0.48<br>+17.64 | +10.40<br>+0.50 |
| 6.5 | A1) 1,2,3,3,5-pentamethyl-3H-indolium iodide, 3.62 g<br>A2) 4-(dimethylamino)-benzaldehyde, 1.72 g<br>$pH_m$: 8.1 | intense pink<br>after decolorizing | untreated hair<br>after dyeing<br>light-pink | +83.30<br>+41.53 | −0.48<br>+66.93 | +10.40<br>+7.15 |

TABLE 6

Coloring Results

| No. | A1) Indole-containing component, pH 8.6<br>A2) Aldehyde-containing component | Shade After Coloring/Decolorizing | | Color Measuring Values | | |
|---|---|---|---|---|---|---|
| | | | | L | a | b |
| 7.1 | A1) 1,2,3,3,5,7-hexamethyl-3H-indolium tetrafluoraborate, 3.33 g<br>A2) 3,5-dimethoxy-4-hydroxy-benzaldehyde, 2.09 g<br>$pH_m$: 7.4 | purple<br>after decolorizing | untreated hair<br>after dyeing<br>white | +83.30<br>+31.90 | −0.48<br>+40.52 | +10.40<br>−2.37 |
| 7.2 | A1) 1,2,3,3,5,7-hexamethyl-3H-indolium tetrafluoroborate, 3.33 g<br>A2) 4-hydroxy-3-methoxy-benzaldehyde, 1.75 g<br>$pH_m$: 7.3 | red<br>after decolorizing | untreated hair<br>after dyeing<br>white | +83.30<br>+41.40 | −0.48<br>+53.50 | +10.40<br>+19.41 |
| 7.3 | A1) 1,2,3,3,5,7-hexamethyl-3H-indolium tetrafluoroborate, 3.33 g<br>A2) 3-hydroxy-4-methoxy-benzaldehyde, 1.75 g<br>$pH_m$: 8.2 | yellow<br>after decolorizing | untreated hair<br>after dyeing<br>white | +83.30<br>+71.97 | −0.48<br>+16.17 | +10.40<br>+70.08 |
| 7.4 | A1) 1,2,3,3,5,7-hexamethyl-3H-indolium tetrafluoroborate, 3.33 g<br>A2) 3,4,5-trihydroxybenzaldehyde 1.98 g<br>$pH_m$: 7.1 | intense wine-red<br>after decolorizing | untreated hair<br>after dyeing<br>greenish | +83.30<br>+24.12 | −0.48<br>+24.20 | +10.40<br>+0.40 |
| 7.5 | A1) 1,2,3,3,5,7-hexamethyl-3H-indolium tetrafluoroborate, 3.33 g<br>A2) 4-(dimethylamino)benzaldehyde, 1.72 g<br>$pH_m$: 8.3 | intense pink<br>after decolorizing | untreated hair<br>after dyeing<br>pinkish | +83.30<br>+54.09 | −0.48<br>+56.26 | +10.40<br>+3.81 |

TABLE 7

Coloring Results

| No. | A1) Indole-containing component, pH 8.6<br>A2) Aldehyde-containing component | Shade After Coloring/Decolorizing | | Color Measuring Values | | |
|---|---|---|---|---|---|---|
| | | | | L | a | b |
| 8.1 | A1) 1,2,3,3,4,7-hexamethyl-3H-indolium tetrafluoroborate, 3.33 g<br>A2) 3,5-dimethoxy-4-hydroxy-benzaldehyde, 2.09 g<br>$pH_m$: 7.4 | wine-red<br>after decolorizing | untreated hair<br>after dyeing<br>white | +83.30<br>+38.72 | −0.48<br>+36.18 | +10.40<br>−2.74 |
| 8.2 | A1) 1,2,3,3,4,7-hexamethyl-3H-indolium tetrafluoroborate, 3.33 g<br>A2) 4-hydroxy-3-methoxy-benzaldehyde, 1.75 g<br>$pH_m$: 7.3 | red<br>after decolorizing | untreated hair<br>after dyeing<br>white | +83.30<br>+47.44 | −0.48<br>+47.58 | +10.40<br>+13.40 |
| 8.3 | A1) 1,2,3,3,4,7-hexamethyl-3H-indolium tetrafluoroborate, 3.33 g<br>A2) 3-hydroxy-4-methoxy-benzaldehyde, 1.75 g<br>$pH_m$: 8.4 | yellow<br>after decolorizing | untreated hair<br>after dyeing<br>white | +83.30<br>+76.06 | −0.48<br>+5.77 | +10.40<br>+59.77 |
| 8.4 | A1) 1,2,3,3,4,7-hexamethyl-3H-indolium tetrafluoroborate, 3.33 g<br>A2) 3,4,5-trihydroxybenzaldehyde 1.98 g<br>$pH_m$: 7.2 | intense wine-red<br>after decolorizing | untreated hair<br>after dyeing<br>yellowish | +83.30<br>+30.30 | −0.48<br>+23.21 | +10.40<br>+1.08 |
| 8.5 | A1) 1,2,3,3,4,7-hexamethyl-3H-indolium tetrafluoroborate, 3.33 g<br>A2) 4-(dimethylamino)benzaldehyde, 1.72 g<br>$pH_m$: 8.4 | intense pink<br>after decolorizing | untreated hair<br>after dyeing<br>pinkish | +83.30<br>+63.61 | −0.48<br>+47.19 | +10.40<br>+7.90 |

TABLE 8

Coloring Results

| No. | A1) Indole-containing component, pH 8.6<br>A2) Aldehyde-containing component | Shade After Coloring/Decolorizing | | Color Measuring Values | | |
|---|---|---|---|---|---|---|
| | | | | L | a | b |
| 9.1 | A1) 5-methoxy-1,2,3,3,-tetra-methyl-3H-indolium iodide, 3.83 g<br>A2) 3,5-dimethoxy-4-hydroxy-benzaldehyde, 2.09 g<br>pH$_m$: 7.8 | wine-red<br><br>after decolorizing | untreated hair<br>after dyeing<br>white | +83.30<br>+22.27 | −0.48<br>+39.15 | +10.40<br>+2.34 |
| 9.2 | A1) 5-methoxy-1,2,3,3-tetra-methyl-3H-indolium iodide, 3.83 g<br>A2) 4-hydroxy-3-methoxy-benzaldehyde, 1.75 g<br>pH$_m$: 7.6 | | untreated hair<br>after dyeing<br>white | +83.30<br>+32.44 | −0.48<br>+56.47 | +10.40<br>+22.50 |
| 9.3 | A1) 5-methoxy-1,2,3,3,tetra-methyl-3H-indolium iodide, 3.83 g<br>A2) 3-hydroxy-4-methoxy benzaldehyde, 1.75 g<br>pH$_m$: 8.7 | orange<br><br>after decolorizing | untreated hair<br>after dyeing<br>white | +83.30<br>+64.11 | −0.48<br>+30.84 | +10.40<br>+74.52 |
| 9.4 | A1) 5-methoxy-1,2,3,3,-tetra-methyl-3H-indolium iodide, 3.83 g<br>A2) 3,4,5-trihydroxybenzaldehyde 1.98 g<br>pH$_m$: 7.5 | intense wine-red<br>after decolorizing | untreated hair<br>after dyeing<br>white | +83.30<br>+19.45 | −0.48<br>+21.11 | +10.40<br>+1.23 |
| 9.5 | A1) 5-methoxy-1,2,3,3,-tetra-methyl-3H-indolium iodide, 3.83 g<br>A2) 4-(dimethylaminobenz-aldehyde, 1.75 g<br>pH$_m$: 8.2 | intense pink<br>after decolorizing | untreated hair<br>after dyeing<br>white | +83.30<br>+48.28 | −0.48<br>+61.52 | +10.40<br>+0.08 |

TABLE 9

Coloring Results

| No. | A1) Indole-containing component, pH 8.4<br>A2) Aldehyde-containing component | Shade After Coloring/Decolorizing | | Color-Measuring Values | | |
|---|---|---|---|---|---|---|
| | | | | L | a | b |
| 10.1 | A1) 5-hydroxy-1,2,3,3,-tetra-methyl-3H-indolium iodide, 3.65 g<br>A2) 3,5-dimethoxy-4-hydroxy-benzaldehyde, 2.09 g<br>pH$_m$: 7.3 | wine-red<br><br>after decolorizing | untreated hair<br>after dyeing<br>white | +83.30<br>+26.90 | −0.48<br>+32.82 | +10.40<br>+4.88 |
| 10.2 | A1) 5-hydroxy-1,2,3,3-tetra-methyl-3H-indolium iodide, 3.65 g<br>A2) 4-hydroxy-3-methoxy-benzaldehyde, 1.75 g<br>pH$_m$: 7.3 | red<br><br>after decolorizing | untreated hair<br>after dyeing<br>white | +83.30<br>+36.67 | −0.48<br>+47.42 | +10.40<br>+24.17 |
| 10.3 | A1) 5-hydroxy-1,2,3,3,-tetra-methyl-3H-indolium iodide, 3.65 g<br>A2) 3-hydroxy-4-methoxy-benzaldehyde, 1.75 g<br>pH$_m$: 8.0 | orange<br><br>after decolorizing | untreated hair<br>after dyeing<br>white | +83.30<br>+58.89 | −0.48<br>+23.29 | +10.40<br>+63.05 |
| 10.4 | A1) 5-hydroxy-1,2,3,3,-tetra-methyl-3H-indolium iodide, 3.65 g<br>A2) 3,4,5-trihydroxy-benzaldehyde, 1.98 g<br>pH$_m$: 7.1 | intense wine-red<br>after decolorizing | untreated hair<br>after dyeing<br>white | +83.30<br>+24.66 | −0.48<br>+24.35 | +10.40<br>+4.62 |
| 10.5 | A1) 5-hydroxy-1,2,3,3,-tetra-methyl-3H-indolium iodide, 3.65 g<br>A2) 4-(dimethylamino)benzal-dehyde, 1.72 g<br>pH$_m$: 8.1 | intense pink<br>after decolorizing | untreated hair<br>after dyeing<br>bright-pink | +83.30<br>+46.09 | −0.48<br>+42.68 | +10.40<br>−2.65 |

TABLE 10

Coloring Results

| No. | A1) Indole-containing component, pH 8.4<br>A2) Aldehyde-containing component | Shade After Coloring/Decolorizing | | Color-Measuring Values | | |
|---|---|---|---|---|---|---|
| | | | | L | a | b |
| 11.1 | A1) 5-hydroxy-1,2,3,3,-tetra-methyl-3H-indolium iodide, 3.65 g<br>A2) 3,5-dimethoxy-4-hydroxy-benzaldehyde, 2.09 g<br>pH$_m$: 9.9 | intense eggplant<br>after decolorizing | untreated hair<br>after dyeing<br>white | +83.30<br>+22.41 | −0.48<br>+25.83 | +10.40<br>−3.60 |
| 11.2 | A1) 5-hydroxy-1,2,3,3-tetra-methyl-3H-indolium iodide, 3.65 g<br>A2) 4-hydroxy-3-methoxy-benzaldehyde, 1.75 g<br>pH$_m$: 10.0 | red<br>after decolorizing | untreated hair<br>after dyeing<br>white | +83.30<br>+31.07 | −0.48<br>+40.01 | +10.40<br>+12.18 |
| 11.3 | A1) 5-hydroxy-1,2,3,3,-tetra-methyl-3H-indolium iodide, 3.65 g<br>A2) 3,4,5-trihydroxybenz-aldehyde, 1.98 g<br>pH$_m$: 9.7 | black<br>after decolorizing | untreated hair<br>after dyeing<br>white | +83.30<br>+17.95 | −0.48<br>+9.23 | +10.40<br>−0.30 |
| 11.4 | A1) 5-hydroxy-1,2,3,3-tetra-methyl-3H-indolium iodide, 3.65 g<br>A2) 4-(dimethylamino)benz-aldehyde, 1.72 g<br>pH$_m$: 10.2 | intense pink<br>after decolorizing | untreated hair<br>after dyeing<br>bright pink | +83.30<br>+29.12 | −0.48<br>+41.38 | +10.40<br>−5.46 |

TABLE 11

Coloring Results

| No. | A1) Indole-containing component, pH 9.2<br>A2) Aldehyde-containing component | Shade After Coloring/Decolorizing | | Color-Measuring Values | | |
|---|---|---|---|---|---|---|
| | | | | L | a | b |
| 12.1 | A1 1,2-dimethyl-5-methoxy-3-(spirocyclohexul-3H-indolium tetrafluoroborate, 0.95 g<br>A2) 3,5,dimethoxy-4-hydroxy-benzaldehyde, 0.52 g<br>pH$_m$ = 8.4 | purple<br>after decolorizing | untreated hair<br>after dyeing<br>white | +83.30<br>+56.75 | −0.48<br>+10.85 | +10.40<br>+1.07 |
| 12.2 | A1 1,2-dimethyl-5-methoxy-3-(spirocyclohexyl)-3H-indolium-tetrafluoroborate, 0.95 g<br>A2) 4-hydroxy-3-methoxy-benzaldehyde, 0.44 g<br>pH$_m$ = 8.4 | red<br>after decolorizing | untreated hair<br>after dyeing<br>white | +83.30<br>+65.23 | −0.48<br>+22.28 | +10.40<br>+9.42 |
| 12.3 | A1 1,2-dimethyl-5-methoxy-3-(spirocyclohexyl)-3H-indolium tetrafluoroborate, 0.95 g<br>A2) 3-hydroxy-4-methoxy-benzaldehyde, 0.44 g<br>pH$_m$ = 9.1 | yellow<br>after decolorizing | untreated hair<br>after dyeing<br>white | +83.30<br>+79.41 | −0.48<br>+4.27 | +10.40<br>+33.94 |
| 12.4 | A1 1,2-dimethyl-5-methoxy-3-(spirocyclohexyl)-3H-indolium-tetrafluoroborate, 0.95 g<br>A2) 3,4,5-trihydroxybenz-aldehyde, 0.49 g<br>pH$_m$ = 8.4 | gray-green<br>after decolorizing | untreated hair<br>after dyeing<br>white | +83.30<br>+55.71 | −0.48<br>−0.25 | +10.40<br>+8.40 |
| 12.5 | A1 1,2-dimethyl-5-methoxy-3-(spirocyclohexyl-3H-indolium tetrafluoroborate, 0.95 g<br>A2) 4-(dimethylamino)-benzaldehyde, 0.43 g<br>pH$_m$ = 9.2 | pink<br>after decolorizing | untreated hair<br>after dyeing<br>white | +83.30<br>+73.66 | −0.48<br>+22.70 | +10.40<br>+6.04 |

The L*a*b* color measurements presented in the foregoing Tables 1 to 11 were determined with a Chromameter II instrument supplied by Minolta.

In the foregoing, L stands for luminosity (namely the lower the L value the higher is the color intensity), whereas a is a measure of the red content of the color (namely the higher the a value the greater is the red content). The b value is a measure of the blue content of the color, the blue content being the greater the more negative the b value.

What is claimed is:

1. Agent for dyeing fibers obtained by mixing two components, if necessary with the addition of an alkalinizing agent or an acid, characterized in that one component (component A2) contains at least one carbonyl compound and the other component (component A1) contains at least one indoline derivative of formula (I) or a 3H-indoline derivative of formula (Ia)

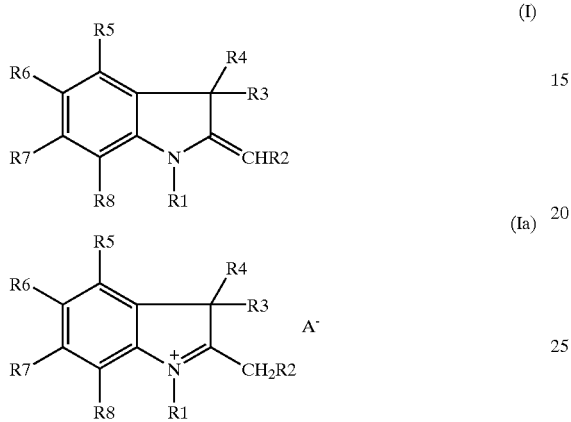

the R1 to R8 and A groups in the formulas (I) and (Ia) having the following meaning:

R1 denotes a straight-chain or branched C1–C8 alkyl group, C1–C8 monohydroxyalkyl group, C2–C8 polyhydroxyalkyl group, C1–C8 alkoxy-(C1–C8)-alkyl group or a thio-(C1–C8)-alkyl group, a —$(CH_2)_n$—X—R group, a —$(CH_2)_m$—X—$(CH_2)_n$—Y—$(CH_2)_p$—$R^a$ group, a —$(CH_2)_p$—$R^a$ group, a —$(CH_2)_m$Y—$(CH_2)_n$—X—$(CH_2)_p$—$R^a$ group, a —$(CH_2)_m$—CO—$(CH_2)_p$—X—$R^a$ group, a —$(CH_2)_m$—X—$(CH_2)_p$—CO—Y—$R^a$ group or

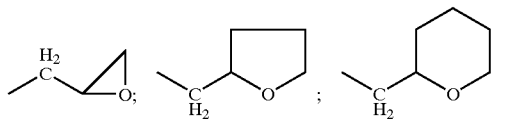

wherein X and Y independently of each other denote an oxygen atom, a sulfur atom or an $NR^b$ group, $R^a$ and $R^b$ independently of each other denote a hydrogen atom, an, optionally substituted, aromatic carbocycle or heterocycle or a straight-chain or branched C1–C8-alkyl group, and n independently of each other denote an integer from 1 to 6 and p denotes an integer from 0 to 6;

R2 is a hydrogen atom or a straight-chain C1 to C6-alkyl group,

R3 and R4 independently of each other denote a straight-chain or branched C1–C4-alkyl group, a $(CH_2)_n$—$R^c$ group, a —$(CH_2)_m$—$CHR^c$—C—X—$(CH_2)_n$—$R^c$ group, a —$(CH_2)_n$—CO—$R^c$ group, a —$(CH_2)_n$—CO—$XR^c$ group, a —$(CH_2)_n$—CN group, a —$(CH_2)_n$—CH=C(CH$_3$)$_2$ group, a —$(CH_2)_m$—X—$CHR^c$—$(CH_2)_n R^c$ group or a —$(CH_2)_n$CH=CH group, X standing for an oxygen atom, sulfur atom or an $NR^b$ group, m and n independently of each other denoting 1 to 6 and $R^c$ standing for a hydrogen atom, an, optionally substituted, aromatic carbocycle or heterocycle or a straight-chain or branched C1–C6-alkyl group, providing that the R3 and R4 groups, together, linked through a $(CH_2)_n$ group (with n=1–3) can also form a spiro compound with the 3H carbon;

R5, R6, R7 and R8 independently of each other denote hydrogen atom, a straight-chain or branched C1–C4-alkyl group or a C1–C4-hydroxyalkyl group, a hydroxyl group, a methoxy group, a benzyl group, a halogen atom, a nitro group, a nitroso group, a cyano group, a trifluoromethyl group, a —CHO group, a —$COR^d$ group, a —COOH group, a —$CO_2R^d$ group, an —$OCOR^d$ group, an —OCH$_2$—aryl group, an —SO$_2$NH$_2$ group, an —NH$_2$ group, an NH$_3^+$ group, an —$NHR^d$ group, an —$NH_2R^{d+}$ group, an —$N(R^d)_2$ group, an —$N(R^d)_3^+$ group, an —$NHCOR^d$ group, an —$NHCOOR^d$ group, a —CH$_2$NH$_2$ group, a —$CH_2NHR^d$ group, a —CH$_2$N$(R^d)_2$ group, a —CO$_2$CF$_3$ group, a —PO(OR$^d$)$_2$ group, an —SO$_2$CHF$_2$ group, an —SO$_2$CF$_3$ group, an —$SO_2R^d$ group or an —$SR^d$ group, wherein $R^d$ denotes a hydrogen atom, an, optionally substituted, aromatic carbocycle or a heterocycle or a C1–C6-alkyl group, providing that at least one of the R5 to R8 groups is different from hydrogen; and A denotes an anion of an organic or inorganic acid.

2. Agent according to claim 1, characterized in that the compound of formula (I)/(Ia) is selected from the group consisting of 1,3,3,4-tetramethyl-2-methyleneindoline and the salts thereof, 1,3,3,5-tetramethyl-2-methyleneindoline and the salts thereof, 1,3,3,6-tetramethyl-2-methyleneindoline and the salts thereof, 1,3,3,7-tetramethyl-2-methyleneindoline and the salts thereof, 1,3,3,6,7-pentamethyl-2-methyleneindoline and the salts thereof, 1,3,3,5,7-pentamethyl-2-methyleneindoline and the salts thereof, 1,3,3,4,7-pentamethyl-2-methyleneindoline and the salts thereof, 5-fluoro-1,3,3-trimethyl-2-methyleneindoline and the salts thereof, 5-isopropyl-1,3,3-trimethyl-2-methyleneindoline and the salts thereof, 5-hydroxy-1,3,3-trimethyl-2-methyleneindoline and the salts thereof, 5-methoxy-1,3,3-trimethyl-2-methyleneindoline and the salts thereof, 5-nitro-1,3,3-trimethyl-2-methyleneindoline and the salts thereof, 5-amino-1,3,3-trimethyl-2-methyleneindoline and the salts thereof, 5-N-acetylamino-1,3,3-trimethyl-2-methyleneindoline and the salts thereof, 6-hydroxy-1,3,3-trimethyl-2-methyleneindoline and the salts thereof, 6-methoxy-1,3,3-trimethyl-2-methyleneindoline and the salts thereof, 5-methoxy-6-nitro-1,3,3-trimethyl-2-methyleneindoline and the salts thereof, 5-methoxy-6-amino-1,3,3-trimethyl-2-methyleneindoline and the salts thereof, 5-methoxy-6-N-acetylamino-1,3,3-trimethyl-2-methyleneindoline and the salts thereof, 5,6-dihydroxy-1,3,3-trimethyl-2-methyleneindoline and the salts thereof, 5,6-dimethoxy-1,3,3-trimethyl-2-methyleneindoline and the salts thereof, 5,6-methylenedioxy-1,3,3-trimethyl-2-methyleneindoline and the salts thereof, 4,5-dihydroxy-1,3,3-trimethyl-2-methyleneindoline and the salts thereof, 5,7-dihydroxy-1,3,3-trimethyl-2-methyleneindoline and the salts thereof, 5-amino-6-methoxy-1,3,3-trimethyl-2-methyleneindoline and the salts thereof, 5-amino-7-hydroxy-1,3,3-trimethyl-2-methyleneindoline and the salts thereof, 5-hydroxy-7-amino-1,3,3-trimethyl-2-methyleneindoline and the salts thereof, 5-hydroxy-7-N-acetylamino-1,3,3-trimethyl-2-methyleneindoline and the salts thereof, 1-methyl-3-spirocyclopropyl-2-methyleneindoline and the salts thereof, 1-methyl-3-spirocyclohexyl-2-methyleneindoline and the salts thereof, 1-methyl-3-spirocyclohexyl-5-hydroxy-2-methyleneindoline and the salts thereof and 1-methyl-3-spirocyclohexyl-5-methoxy-2-methyleneindoline and the salts thereof.

3. Agent according to claim 1, characterized in that the carbonyl compound is selected from the group consisting of anillin, isovanillin, 3,4-dihydroxybenzaldehyde, 4-hydroxybenzaaldehyde, 3,5-dimethoxy-4-hydroxybenzaldehyde, droxybenzaldehyde, 4-dimethylaminobenzaldehyde, 4-methyl-5-imidazolecarboxaldehyde, 4-dimethyl-aminocinnamaldehyde, 4-hydroxy-2-methoxybenzaldehyde, 3,5-dimethyl-4-hydroxybenzaldehyde, 4-dimethylamino-2-methoxybenzaldehyde, 2-hydroxybenzaldehyde, 4-hydroxy 1-naphthaldehyde, 4-methoxy-1-naphthaldehyde, 4-dimethylamino-1-naphthaldehyde, 4'-hydroxybiphenyl-1-carboxaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, indole-3-carboxaldehyde, benzene-1,4-dicarboxaldehyde, 4-ethoxybenzaldehyde, 2-methyl-1,4-naphthoquinone, 4-carboxybenzaldehyde, 4-hydroxy-3-methoxycinnamaldehyde, 3,5-dimethoxy-4-hydroxycinnamaldehyde, 3-methoxy-4-(1-pyrrolidinyl)benzaldehyde, 4-dimethylamino-3-methoxy-benzaldehyde, 1,2,-phthalaldehyde, pyrrole-2-aldehyde, thiophene-2-aldehyde, thiophene-3-aldehyde, chromone-3-carboxaldehyde, 6-methyl-4-oxo-1(4H)-benzopyran-3-carboxaldehyde, N-methylpyrrole-2-aldehyde, 5-methylfufural, 6-hydroxychromene-3-carboxyaldehyde, 6-methyl-indole-3-carboxaldehyde, 4-dibutylaminobenzaldehyde, N-ethylcarbazole-3-aldehyde, 4-diethyl-amino-2-hydroxybenzaldehyde, 3,4-dimethoxy-5-hydroxybenzaldehyde, 5-[4-(dimethylamino)phenyl]-2,4-pentadienal, 2,3-thiophenecarboxaldehyde, 2,5-thiophenedicarboxaldehyde, 2-methoxy-1-naphthaldehyde, 3-ethoxy-4-hydroxybenzaldehyde, 2-nitrobenzaldehyde, 3-nitrobenzaldehyde and 4-nitrobenzaldehyde.

4. Agent according to claim 1, characterized in that the total amount of the compound of formula (I) or (Ia) contained in component A1 is about 0.02 to 20 weight percent.

5. Agent according to claim 1, characterized in that the total amount of the carbonyl compound contained in component A2 is about 0.02 to 20 weight percent.

6. Agent according to claim 1, characterized in that the total amount of the compound of formula (I) or (Ia) and the carbonyl compound contained in the agent obtained by mixing components A1 and A2 is about 0.01 to 10 weight percent.

7. Agent according to claim 1, characterized in that it contains additionally at least one direct dye.

8. Agent according to claim 1, characterized in that the pH of the agent is between 3 and 11.

9. Multicomponent kit for dyeing and later decolorizing fibers, characterized in that it contains a colorant (A) according to claim 1 and at least one sulfite-containing, decolorizing component (B).

10. Multicomponent kit according to claim 9, characterized in that the decolorizing agent (B) has a pH of 3 to 8.

* * * * *